(12) United States Patent
Marcus et al.

(10) Patent No.: US 10,271,727 B2
(45) Date of Patent: Apr. 30, 2019

(54) WIRELESS ECG SENSOR SYSTEM AND METHOD

(71) Applicant: Medicomp, Inc., Melbourne, FL (US)

(72) Inventors: Sean Marcus, Rockledge, FL (US); Chris Chang, New Albany, OH (US); Scott Baskerville, Melbourne Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 0 days.

(21) Appl. No.: 15/839,996

(22) Filed: Dec. 13, 2017

(65) Prior Publication Data

US 2018/0098698 A1 Apr. 12, 2018

Related U.S. Application Data

(62) Division of application No. 14/644,300, filed on Mar. 11, 2015, now Pat. No. 10,098,544.

(51) Int. Cl.
*A61B 5/00* (2006.01)
*A61B 5/0452* (2006.01)
(Continued)

(52) U.S. Cl.
CPC ............ *A61B 5/0006* (2013.01); *A61B 5/002* (2013.01); *A61B 5/0022* (2013.01);
(Continued)

(58) Field of Classification Search
CPC .............. A61B 5/04012; A61B 5/0402; A61B 5/04085; A61B 5/6833; A61B 5/0006;
(Continued)

(56) References Cited

U.S. PATENT DOCUMENTS

| 2006/0066449 A1* | 3/2006 | Johnson | A61B 5/1113 340/539.12 |
| 2012/0215076 A1* | 8/2012 | Yang | A61B 5/0205 600/301 |

OTHER PUBLICATIONS

USPTO Non-Final Office action in related U.S. Appl. No. 14/644,300 dated Feb. 27, 2018 (11 pages).

* cited by examiner

*Primary Examiner* — Christopher Koharski
*Assistant Examiner* — Pamela M Bays
(74) *Attorney, Agent, or Firm* — Mark Malek; Kelly G. Swartz; Widerman Malek, PL

(57) ABSTRACT

A system for monitoring cardiac health of a user including a local sensing subsystem, a contactless interrogation subsystem, and a remote monitoring subsystem. The local sensing subsystem may include a sensor patch configured to attach to the user and include a substrate, a passive radio-frequency identification transponder, and a first antenna. The contactless interrogation subsystem may include an interrogator separated from the sensor patch, which may include a second antenna, a demodulator, and a communications link. The remote monitoring subsystem may include a computing system comprising a processor for executing instructions. The local sensing subsystem may be adapted to perform at least one scan. The contactless interrogation subsystem may be adapted to operate the demodulator to receive a cardiac event and to operate the communications link to transmit the cardiac event. The remote monitoring subsystem may be adapted to execute the instructions to detect an arrhythmia from the cardiac reading.

6 Claims, 5 Drawing Sheets

(51) Int. Cl.
*A61B 5/0402* (2006.01)
*A61N 1/372* (2006.01)
*A61B 5/0404* (2006.01)
*A61B 5/04* (2006.01)
*A61B 5/0408* (2006.01)
*A61B 5/0428* (2006.01)
*A61N 1/04* (2006.01)
*G06F 19/00* (2018.01)
*G16H 40/67* (2018.01)
*G16H 15/00* (2018.01)
*G16H 10/60* (2018.01)

(52) U.S. Cl.
CPC .......... *A61B 5/0024* (2013.01); *A61B 5/0402* (2013.01); *A61B 5/0404* (2013.01); *A61B 5/04012* (2013.01); *A61B 5/0452* (2013.01); *A61B 5/04085* (2013.01); *A61B 5/04087* (2013.01); *A61B 5/04286* (2013.01); *A61B 5/6898* (2013.01); *A61B 5/7228* (2013.01); *A61N 1/0492* (2013.01); *A61N 1/3727* (2013.01); *A61N 1/37288* (2013.01); *G06F 19/00* (2013.01); *G16H 40/67* (2018.01); *A61B 5/6833* (2013.01); *A61B 2560/0214* (2013.01); *A61B 2560/0219* (2013.01); *A61B 2562/08* (2013.01); *G06F 19/3418* (2013.01); *G16H 10/60* (2018.01); *G16H 15/00* (2018.01)

(58) Field of Classification Search
CPC ... A61B 5/0024; A61B 5/7228; A61B 5/0404; A61B 5/0022; A61N 1/0492; A61N 1/3737; A61N 1/3788; G06F 19/3418
See application file for complete search history.

WIRELESS ECG SENSOR SYSTEM AND METHOD

CROSS-REFERENCE TO RELATED APPLICATIONS

The present application is a divisional of U.S. patent application Ser. No. 14/644,300 titled Wireless ECG Sensor System and Method and filed on Mar. 11, 2015, now U.S. Pat. No. 10,098,544, the entire content of which is incorporated herein by reference.

FIELD OF THE INVENTION

The present invention relates to systems and methods relating to wireless electrodes used to detect electrical signals from a subject patient.

BACKGROUND

Conventionally, electrodes are attached to a patient's skin and used for detecting electrical impulses in a patient. These electrical impulses may be used, for example, to produce an electrocardiogram (ECG).

These conventional electrodes have wired connections extending from the electrode a receiving device. The electrical signal received by the electrode is sent along a wire and is then amplified and read by the receiving device. Thus, while an ECG is being taken, the patient must remain physically connected to the monitoring device.

The use of wired connections means that the electrode may become unplugged due to patient or other movement. Also, having wired connections tethers a patient to a particular piece of machinery, limiting patient mobility or requiring suspending detection using the electrodes if the patient is moved away from the receiving device. This can be an issue when transporting the patient, particularly in transition between an ambulance and a healthcare facility, or indeed within a healthcare facility.

There is also an issue with patient compliance wearing wired electrodes, as this causes discomfort and unease to the patient. A lack of compliance with electrode monitoring (e.g., disconnecting the wire from the electrode by the patient) means a break in monitoring and possible error or alert messages being sent to the medical staff. Accordingly, there is a need in the art for a solution for performing an ECG that addresses the issues presented by requiring a wired connection.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to wireless electrode systems and methods which may provide more reliable signal monitoring from an electrode and improved data collection abilities.

An exemplary aspect of the invention is directed toward a wireless ECG sensor system including a sensor patch configured to attach to a user and an interrogator device separated from the sensor patch and configured to be carried by a housing. The sensor patch may include a substrate having first and second sections and configured to exhibit dielectric dispersion between the first and the second sections. The positive electrode may be carried by the first section of the substrate, and a negative electrode maybe carried by the second section of the substrate. The sensor patch may also include a passive radio-frequency identification (RFID) transponder carried by the substrate.

The RFID transponder may include a first antenna, a non-transitory and non-volatile storage medium in electrical communication with the first antenna, a load modulation switch in electrical communication with the first antenna, and a microcontroller in electrical communication with the first antenna and in data communication with both the storage medium and the load modulation switch.

The interrogator device may include a second antenna in electrical communication with a power source and configured to wirelessly transmit electromagnetic radiation having a resonant frequency of the first antenna of the sensor patch, and a demodulator configured to measure a voltage amplitude of the electromagnetic radiation wirelessly transmitted by the second antenna.

The first antenna of the sensor patch may be configured to inductively receive power for operating the passive RFID transponder of the sensor patch from the electromagnetic radiation wirelessly transmitted by the second antenna of the interrogator device. Upon receipt of power, the microcontroller of the sensor patch is configured to receive a cardiac activity signal from at least one of the positive and negative electrodes of the sensor patch, to retrieve a location identifier from the storage medium of the sensor patch, and to operate the load modulation switch of the sensor patch to alter the voltage amplitude of the electromagnetic radiation to transmit to the demodulator a cardiac event reading comprising the cardiac activity signal and the location identifier.

In some embodiments, the sensor patch may include an analog-to-digital converter carried by the substrate. In these embodiments, at least one of the positive and negative electrodes may be configured to transmit the cardiac activity signal in analog format to the analog-to-digital converter; and the analog-to-digital converter is configured to convert the cardiac activity signal from analog format to digital format and to transmit the cardiac activity signal in digital format to the microcontroller.

The sensor patch may also include an amplifier and an analog-to-digital converter both carried by the substrate. In some embodiments, at least one of the positive and negative electrodes is configured to transmit the cardiac activity signal in analog format to the amplifier. The amplifier may be configured to amplify the cardiac activity signal to an amplified form to define an amplified cardiac activity signal, and to transmit the amplified cardiac activity signal to the analog-to-digital converter. The analog-to-digital converter may be configured to convert the amplified cardiac activity signal from analog format to digital format and to transmit the amplified cardiac activity signal in digital format to the microcontroller.

The first antenna of the sensor patch may be configured to inductively receive power from the electromagnetic radiation wirelessly transmitted by the second antenna of the interrogator device when the second antenna is positioned a distance of less than one meter from the first antenna of the sensor patch.

The electromagnetic radiation wirelessly transmitted by the second antenna may be characterized by a frequency selected from the group consisting of LF band (120-150 kHz) and HF band (13.56 MHz). The power source comprises at least one of a battery and a power cable.

The power inductively received by the first antenna of the sensor patch may be an AC input voltage. The RFID transponder of the sensor patch may also include at least one of a converter and a regulator, where the converter is configured to convert the AC input voltage to a DC output voltage, and where the regulator is configured to sustain the DC output voltage within a target DC bias range.

The microcontroller of the sensor patch may also be configured to store the cardiac activity signal on the storage medium of the sensor patch.

In some embodiments, the first antenna of the sensor patch may be configured to receive the location identifier from the electromagnetic radiation wirelessly transmitted by the second antenna, and to store the location identifier on the storage medium. In addition, the sensor patch may also be configured to receive a patch identifier from the electromagnetic radiation wirelessly transmitted by the second antenna, and to store the patch identifier on the storage medium of the sensor patch.

The interrogator device may include a communications link in data communication with the demodulator and with at least one of a wired local area network (LAN) and a wireless LAN. The demodulator may be configured to transmit the cardiac event reading to a computing system through the communications link. In some embodiments, the computing system may include a mobile phone. The computing system may be configured to detect an arrhythmia from the respective cardiac event readings transmitted by at least one of the plurality of sensor patches.

In some embodiments a plurality of sensor patches are used. The resonant frequency of the first antenna of each of the plurality of sensor patches may be configured to be distinct from the respective resonant frequency of the first antenna of each of the other sensor patches, and the interrogator device may be configured to wirelessly transmit electromagnetic radiation having a plurality of transmission frequencies such that at least one of the plurality of the transmission frequencies equals the respective resonant frequency of the first antenna of at least one of the plurality of sensor patches.

In some embodiments, each of the plurality of sensor patches is configured to be positioned on the user according to an ECG electrode placement methodology selected from a group including standard 3-lead (Einthoven's Triangle), modified central lead (MCL1), standard 5-lead using Lead V1, standard 5-lead using Lead V5, EASI™ 5-lead, and interpolated 12-lead.

Some embodiments of the invention may include a remote monitoring subsystem including a computing system having a processor for executing instructions stored in a non-transitory computer readable memory.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention text, as shown and described by the various figures and accompanying text, provides a wireless sensor system which can be used to detect electrical impulses from a patient's body. For instance, the system may be used to gather information for an electrocardiogram of the patient.

FIGS. 1-8 illustrate exemplary embodiments of wireless ECG sensors and related systems and methods.

Figure 1:
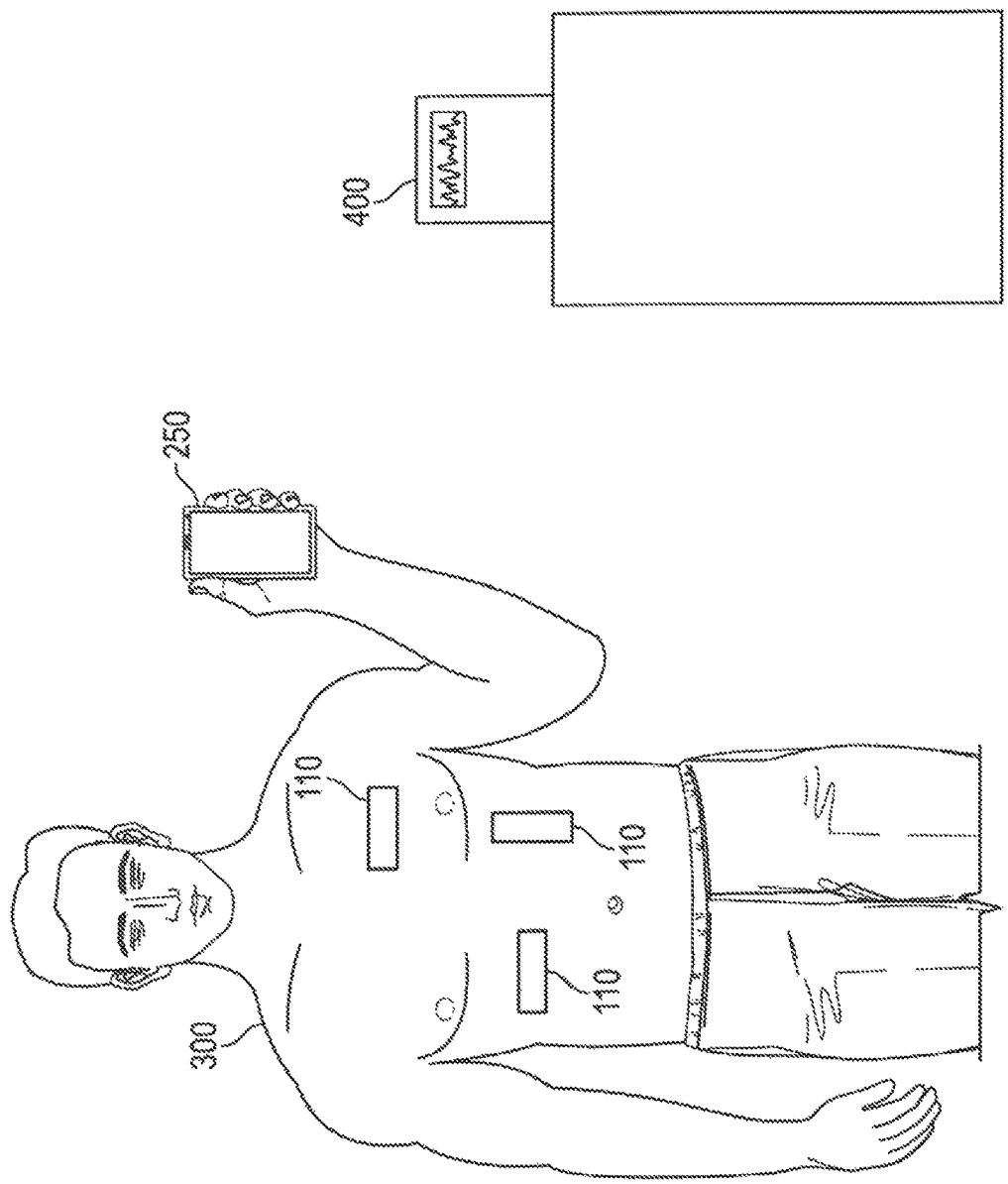
FIG. 1 is a perspective view of a patient and an ECG sensor system according to an embodiment of the present invention.

As illustrated in FIG. 1, an exemplary embodiment of the invention includes an ECG sensor 110 and an interrogator device 250 separate from the ECG sensor 110. In use, the ECG sensor 110 may be attached to a patient 300.

The ECG sensor 110 may be powered by receiving a signal from the interrogator device 250. The powered ECG sensor 110 may then detect an electrical signal from the patient 300, and send information to the interrogator device 250. The interrogator device 250 may then transmit the information from the ECG sensor 110 to a monitoring system 400.

Figure 2:
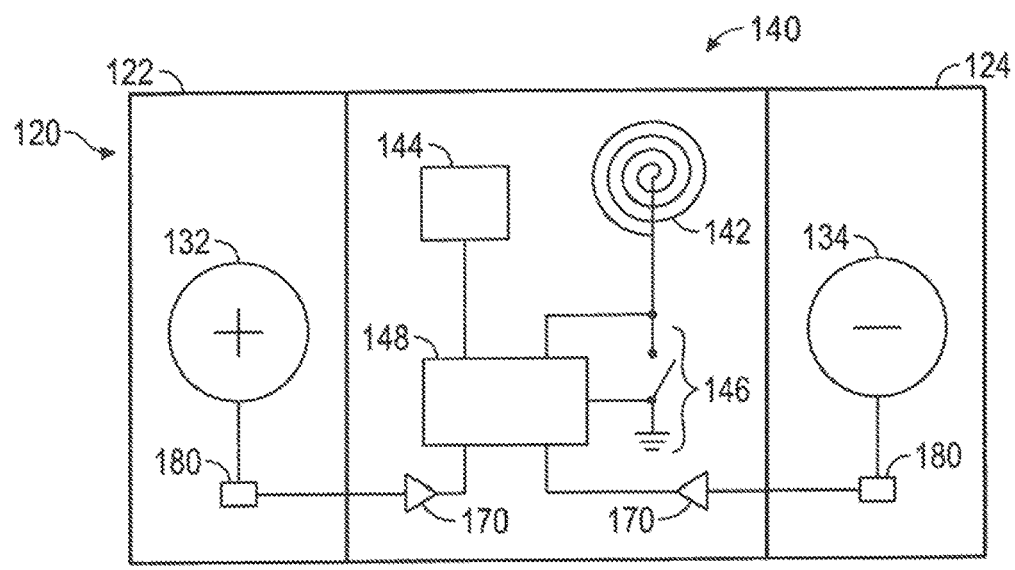
FIG. 2 is diagram, from a top view, of an exemplary embodiment of the ECG sensor of FIG. 1.
Figure 3:
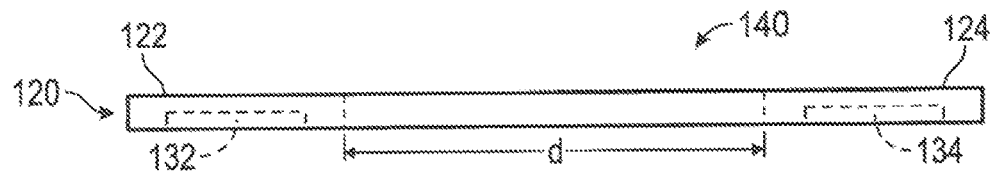
FIG. 3 is a side view of the ECG sensor of FIG. 1.

As illustrated in FIGS. 2 and 3, the ECG sensor 110 may include a substrate 120 having a first section 122 and a second section 124 formed so as to exhibit a dielectric dispersion therebetween. First section 122 may include a positive electrode 132 and the second section 124 may include a negative electrode 134. The substrate 120 also includes a radio frequency identification device (RFID) 140. The RFID 140 may be disposed between the positive electrode 132 and the negative electrode 134 on a third section 126 of the substrate 120, or in any other suitable location on the substrate 120. The substrate may be formed of any desired material. In some embodiments, the substrate 120 will have a low electrical conductivity (e.g., plastic, fabric, etc.).

For example, as illustrated in FIG. 2, the electrodes 132 and 134 are separated by a non-conductive portion of the substrate on which the RFID 140 is formed (e.g., the third section 126). By so doing, a difference in potential can be detected between the electrodes 132 and 134.

It is noted that the substrate 120 may formed as a patch which can be adhered to a patient's body. Thus, the application of the ECG sensor 110 to the patient may be done similarly to that of a conventional ECG sensor patch.

While the term RFID is used to describe an exemplary operation of a circuit used in the ECG sensor 110, the invention is not limited to conventional RFID chips. As illustrated in FIG. 2, the RFID 140 may include an antenna 142 connected to a micro controller 148 and a load modulation switch 146. The micro-controller 148 may also be connected to the load modulation switch 146, an external memory 144, and an analog/digital controller (ADC) 170. The ADC(s) 170 may be connected to the positive electrode 132 and the negative electrode 134.

The antenna 142 may be configured so as to resonate when a certain frequency of electromagnetic signal is received. When the antenna 142 receives the correct frequency, power is generated within the antenna 142 and used to power microcontroller 148 and other components of ECG sensor 110. The structure of antenna 142 is not particularly limited and may include, for example, a metal coil formed so as to resonate at a specific frequency. The antenna 142 may inductively receive power as an AC signal. The antenna 142 may also include a power converter to convert the power received to a DC signal. The antenna 142 may also include a regulator connected to the power converter so as to sustain the DC output voltage within a target DC bias range.

The microcontroller 148 may communicate with memory 144. The memory 144 may be integral with the microcontroller 148 or may be external to the microcontroller 148. The memory 144 may include software for the microcontroller 148, and may also be used to store data collected from the electrodes 132 and 134, ECG sensor identification information, antenna signal reception timing information, location data, etc. The memory 144 can be persistent (e.g., non-volatile), so as to retain information when power is not applied to the ECG sensor 110. Thus, memory 144 may be a non-volatile and non-transitory medium.

As noted above, the microcontroller 148 may also be connected, directly or indirectly, to the electrodes 132 and 134. In some embodiments, the microcontroller 148 is connected to one or more of the ADC 170, which is then connected to the electrodes 132 and 134. The ADC 170 reads differences in the voltage across the electrodes 132 and 134 over time and converts the detected analog signals to digital signals. Optionally, an amplifier 180 may also be included on the substrate 120. The amplifier 180 may be located between one or both of the electrodes 132 and 134 and the corresponding ADC(s) 170.

During normal operation, power is supplied to microcontroller 148 from a signal received by the antenna 142. As an electrical signal is picked up from the body through the electrodes 132 and 134 and converted by the ADC 170, the electrical signal is sent to the microcontroller 148.

The detected ECG signal may then be transmitted by the antenna 142 through the use of the load modulation switch 146 controlled by the microcontroller 148. In addition, other information can also be sent through the antenna 142 through the use of the load modulation switch 146. The other information which may be transmitted is not particularly limited and may include identification information for the ECG sensor 110, sample rate of the ECG data, etc. Indeed, memory 144 may be used to store received location information (e.g., chest-left side), which may be programmed in or received from the interrogator 250, so that the location information may be transmitted along with the identification information of the ECG sensor 110. The information may be sent continuously or at intervals in a data packet.

FIG. 3 illustrates a simplified side view of an ECG sensor 110. As can be seen in the Figure, the electrodes 132 and 134 may be located in first section 122 and second section 124 of substrate 120, respectively. The first and second sections 122 and 124 are separated by a distance D. Distance D is large enough so that a dielectric dispersion is formed between the first section 122 and the second section 124, and in particular between the electrodes 132 and 134. Thus, D is large enough so that a potential difference may be detected between the electrodes 132 and 134. Alternatively, the distance D may be calculated based on the minimum distance between the electrodes 132 and 134, instead of based on the distance between the sections on which the electrodes are located.

Figure 4:
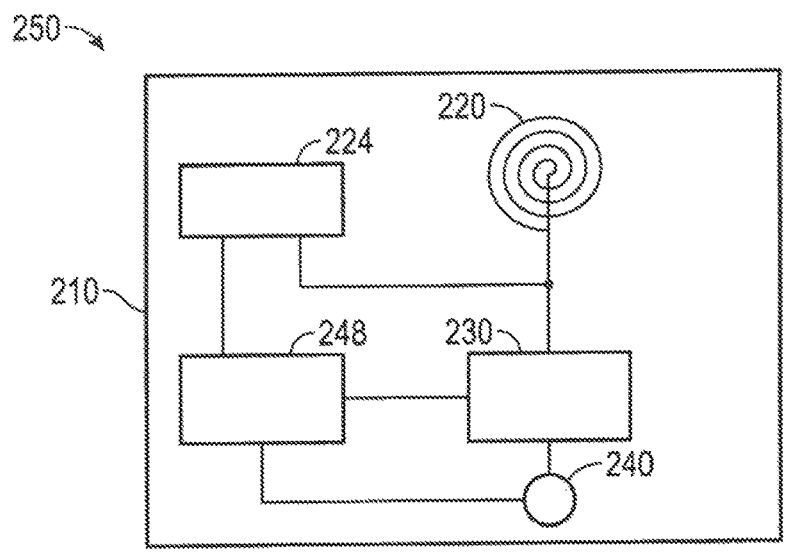
FIG. 4 is a diagram of an exemplary embodiment of the interrogator of FIG. 1.

FIG. 4 illustrates an embodiment of the interrogator device 250. The interrogator device 250 may be configured to both drive/power the ECG sensor 110 through the emission of an electromagnetic signal which is received by ECG sensor 110 through antenna 142, and to receive ECG and other data transmitted from the ECG sensor 110.

The interrogator device 250 may include a housing 210, an antenna 220 connected to a power supply 224, a microcontroller 248, and a demodulator 230. The demodulator 230 and/or the microcontroller 248 may also be connected to a communications link, such as a wireless transmitter 240. The microcontroller 248 may be connected to and control the power supply 224, the demodulator 230 and the wireless transmitter 240. While exemplary embodiments have been described using particular components, the interrogator device 250 may be modified to have any components which are able to transmit an electromagnetic signal to an ECG sensor 110, receive an electromagnetic signal from the ECG sensor 110, and store or pass-on the received data from the electromagnetic signal from the ECG sensor 110. Thus, any form of transmitter/receiver may be used in embodiments of the invention.

In one exemplary embodiment, the antenna 220 is driven so as to emit a signal at a certain frequency or frequencies which may power one or more ECG sensors 110. The antenna 220 is also configured to receive signals from one or more of the ECG sensors 110.

The demodulator 230 reads the return signal(s) from the antenna 220. The demodulator 230 may also include a microprocessor to analyze and process the information received by the antenna 220 or this may be done by the microcontroller 248. One example may include reading the ECG sensor 110 identification information and sending the ECG data identified as belonging to a certain sensor to the wireless transmitter 240. The wireless transmitter 240 may then send the information to the monitoring system 400. The method of sending the information to the monitoring system 400 is not particularly limited. For instance, the transmission may be done through a wireless network connection, Bluetooth, infrared, radio frequency, sonically, etc. The monitoring system 400 may be an ECG reader, a personal computer, a mobile phone, etc.

The monitoring system 400 may be configured to detect certain patterns in the ECG signals. For instance, the monitoring system 400 may be configured to detect an arrhythmia, a pulse rate, or any other cardiac or biological event which may be detected from the ECG signals.

The interrogator 250 may emit electromagnetic radiation to the ECG sensor 110 at any appropriate frequency. For instance, in some embodiments, the antenna 220 may be characterized by emitting a frequency selected from the LF band (120-150 kHz) and HF band (13.56 MHz).

The power supply 224 may be a battery or some other energy storage device. It is also possible to utilize a power cord and external power for direct power and/or recharging the power supply 224.

While the ECG sensor 110 has been described as using a load modulation switch 146, the invention is not limited to such an embodiment. One of ordinary skill in the art would understand that the signal may be sent using other means such as amplitude modulation, frequency modulation, Wi-Fi protocols, etc.

By having the wireless ECG sensors 110 communicating with and being powered by the interrogator device 250, it allows the patient to be monitored without being physically connected to any associated machinery. This may ease the performance of hospital procedures, make physical activities more convenient for the patient, and increase compliance with wearing ECG monitoring devices.

The distance at which the interrogator device 250 can power the ECG sensors 110 is not particularly limited and may be adjusted based on the signal, power, possible interference, and other needs of the patient and/or health care provider. For instance, the interrogator 250 may be configured so as to transmit power to the ECG sensors 110 at a distance of one or more meters away. Alternatively, the interrogator 250 may be configured to power the ECG sensors 110 at distances of less than six inches away.

Figure 5:
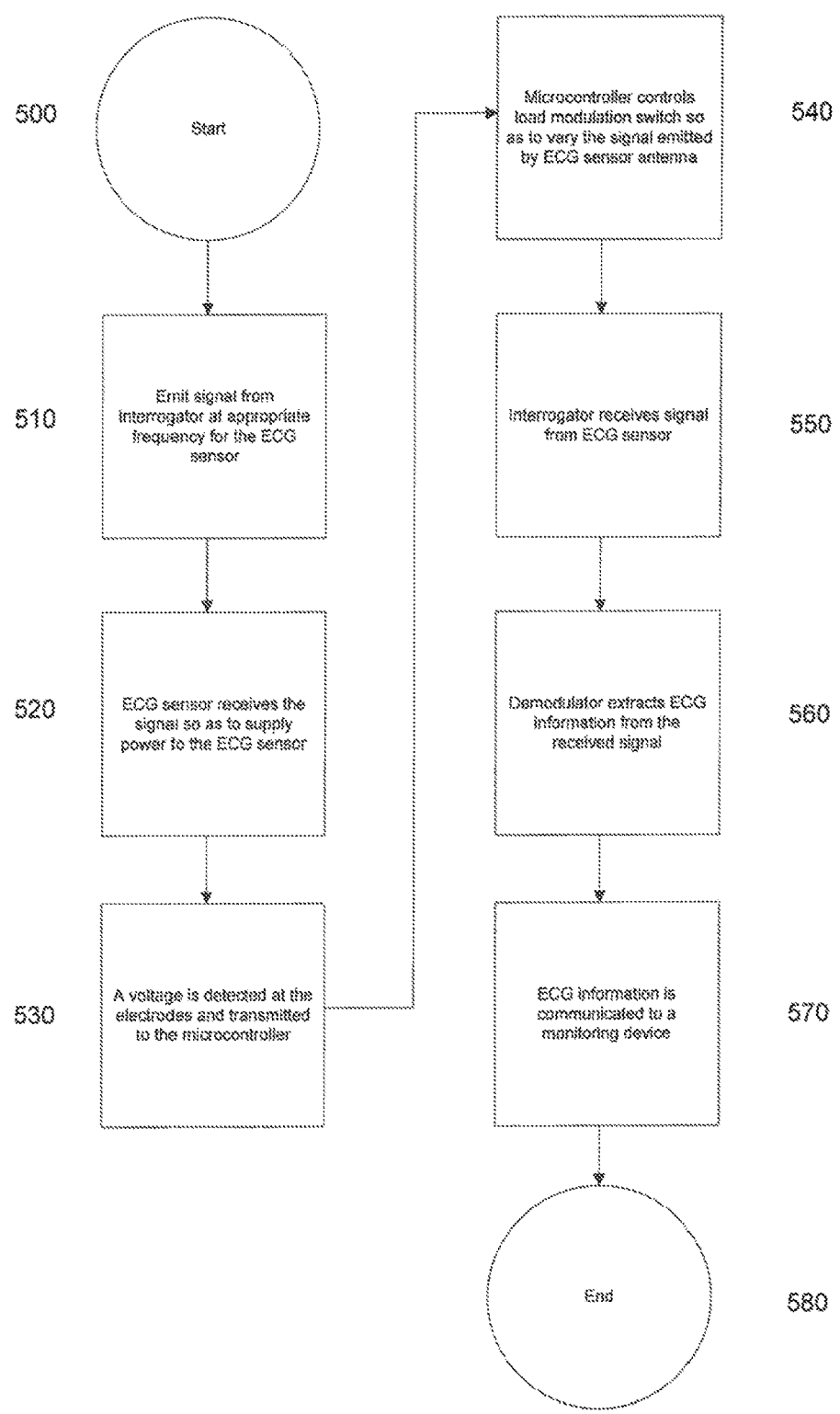
FIG. 5 illustrates an exemplary method associated with the ECG sensor system.

FIG. 5 illustrates an exemplary method of operation of the wireless ECG system. The method starts at block 500. At block 510, a signal is emitted from the interrogator device. The signal transmitted will be such that it will cause a resonance in at least one ECG sensor antenna. At block 520, the ECG sensor receives the signal from the interrogator device which causes the antenna of the ECG sensor to resonate and generate power. At block 530, an electrical signal is detected by the electrodes. This signal may be amplified and/or converted using an ADC prior to reaching the microcontroller. At block 540, the microcontroller controls the load modulation switch so as to vary the signal emitted by the ECG sensor antenna, thereby transmitting information to the interrogator device. At block 550, the interrogator receives the transmission from the ECG sensor. At block 560, the demodulator extracts ECG information, and any other embedded information, from the transmission. At block 570, the ECG information and any other desired information is transmitted to a monitoring device. The method ends at block 580.

The method of use and application of the ECG sensors 110 is not particularly limited and would be understood by one of ordinary skill in the art. For instance, each of the plurality of sensor patches may be positioned on the user according to an ECG electrode placement methodology including but not limited to, the standard 3-lead (Einthoven's Triangle), the modified central lead (MCL1), the standard 5-lead using Lead V1, the standard 5-lead using Lead V5, EASI™ 5-lead, and the interpolated 12-lead methodologies.

While some of the embodiments are described as the interrogator sending and receiving signals to a single ECG sensor 110, this is done for simplicity and the invention is not limited to such. For instance, the interrogator may send signals on a plurality of frequencies where different frequencies resonate with different ECG sensors 110. Similarly, the return signal from the ECG sensors may be propagated on different frequencies so that multiple sensors can be differentiated. It is also possible that all ECG sensors 110 may have antennas 142 tuned to different frequencies and the interrogator 250 emits signals at frequencies for each of the ECG sensors 110. The interrogator may include multiple antennas 220 which can emit a plurality of frequencies at the same time, may have a single antenna emit multiple frequencies in sequence, or some combination thereof.

In addition, in some embodiments, multiple ECG sensors 110 may be resonated/powered with a single frequency. The ECG sensors 110 may then embed identification information in the control signal, or otherwise alter the signal, so that when the signals from the ECG sensors 110 are received by the interrogator 250 it can be differentiated which signals are from which ECG sensor 110. This may be done by signal modulation, the first portion of the transmission may be ECG sensor information and the second portion may be ECG signal data, or any other suitable means as would be understood by one of ordinary skill in the art.

Figure 6:
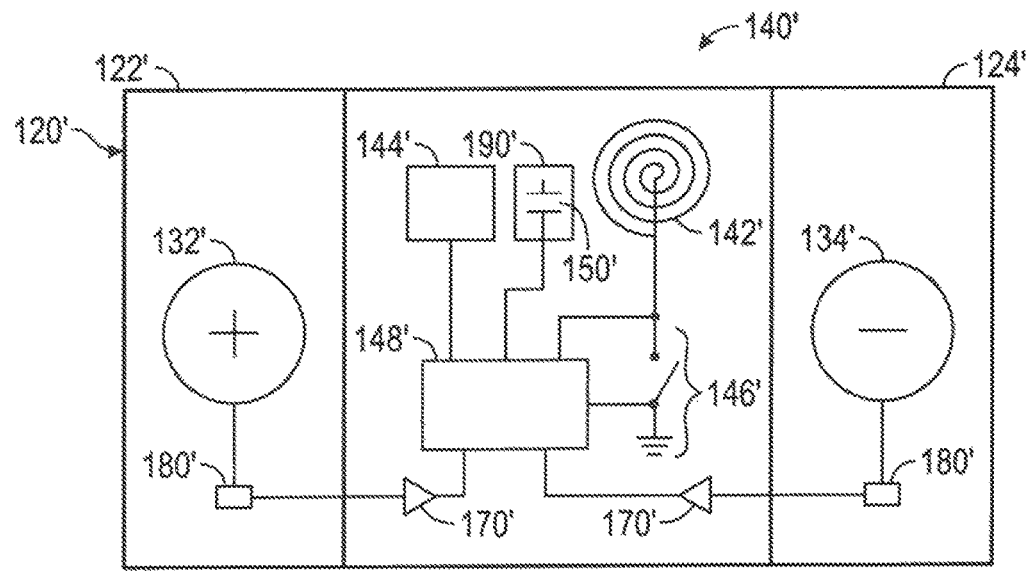
FIG. 6 is diagram, from a top view, of another exemplary embodiment of the ECG sensor of FIG. 1.
Figure 7:
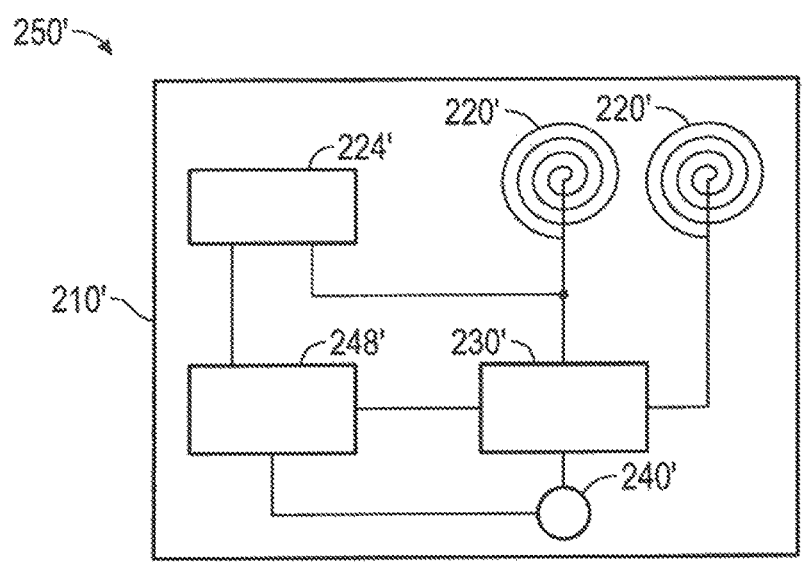
FIG. 7 is diagram of another exemplary embodiment of the interrogator of FIG. 1.

As illustrated in FIGS. 6 and 7, some embodiments of the invention may include a power storage circuit 190'. Referring now to FIGS. 6 and 7, the power storage circuit 190' and related elements will be discussed. All other elements are similar to those of FIGS. 1-5. Thus, like elements will be labeled with a prime symbol (e.g., 250') and will not be discussed.

The inclusion of a power storage circuit 190' in the ECG sensor 110' may allow the storage of information and power while the ECG sensor 110' is not being powered by the signal from the interrogator 250'. This may allow a reduction in power consumption by reducing the scan rate of the interrogator 250'. Generally, the minimum scan rate for an ECG is around 868 MHz in order to detect heart rate and other information. However, other scan rates are possible depending on the signal analysis being conducted.

During normal operation, the interrogator 250' sends signals which resonate with the antenna 142' of a particular ECG sensor 110' at regular or irregular intervals. These signals power the ECG sensor 110' and resonate in the antenna 142' so as to transmit information back to the interrogator 250'. At the same time, some of the power generated by the antenna 142' may be stored in a capacitor 150'. When the antenna 142' is not receiving a signal, and thus not generating power for the ECG sensor 110', the electrical signal detected by the electrodes 132' and 134' can still be stored, for example in memory 144', by using the power stored in the power storage circuit 190'. When the ECG sensor 110' receives a signal from the interrogator 250' again, it can transmit the stored signals and the currently detected signals. In some embodiments the signals may be time stamped, or otherwise ordered, when transmitted. In some embodiments, the data may be transmitted to the interrogator 250' in a first in first out system.

In some embodiments, the microcontroller 148' may detect if the capacitor 150' has enough energy to send a transmission (e.g., activate the load modulation switch 146'), continue monitoring the electrodes 132' and 134', etc. If enough energy is not present, the microcontroller 148' may adjust its actions accordingly. For instance, if enough energy is not present to activate the load modulation switch 146', then the data may be saved to the memory 144' and the load modulation switch 146' may not be activated at that time.

By having an ECG sensor 110' which does not have to be constantly driven/powered by the signal from the interrogator 250', it may allow power savings due to fewer signals being transmitted by the interrogator 250', and thus a longer battery life for the interrogator 250'. The ability of the ECG sensor 110' being able to retain power may also be used so that the interrogator 250' can send signals at different frequencies to different ECG sensors 110' separately in sequence, in order to reduce interference from other ECG sensors 110' or make it easier to identify which ECG sensor 110' is sending the information to the interrogator 250'.

Optionally, the capacitor 150' may be replaced or augmented with a rechargeable or non-rechargeable battery, or some other energy storage mechanism, so as to provide a longer or more reliable and persistent charge.

In some embodiments, as shown in FIG. 7 and described above, the interrogator 250' may have multiple antennas 220' which may each emit one or more different frequencies. Thus, the interrogator 250' can power and receive signals from multiple ECG sensors 110' operating on different frequencies at the same time. This can allow higher scan rates than would be possible by sending different frequencies sequentially from only one antenna 220'. The interrogator 250' may have a different antenna 220' for each frequency, or may transmit multiple frequencies over the same antenna 220'.

Figure 8:
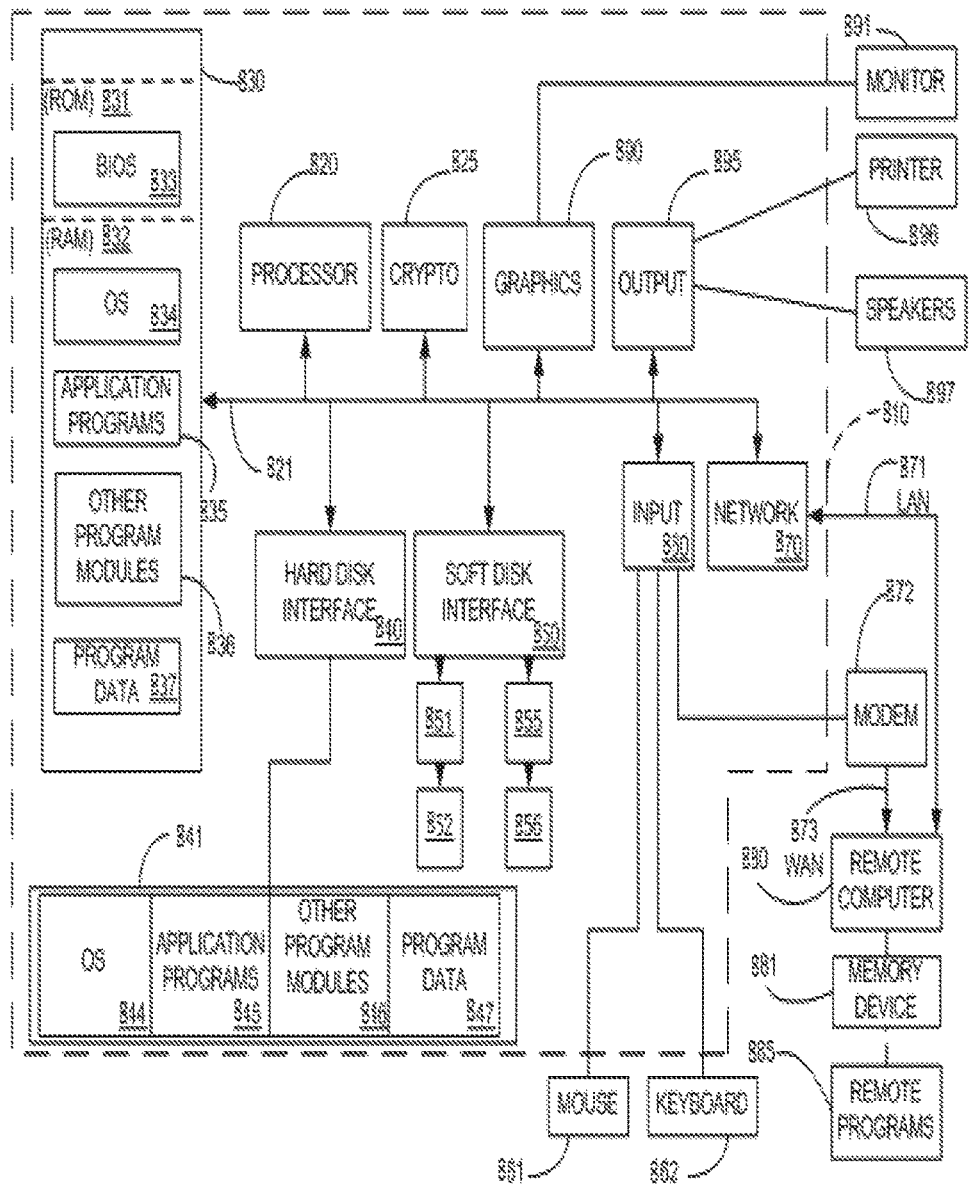
FIG. 8 illustrates an exemplary computer system.

A skilled artisan will note that one or more of the aspects of the present invention may be performed on a computing device. The skilled artisan will also note that a computing device may be understood to be any device having a processor, memory unit, input, and output. This may include, but is not intended to be limited to, cellular phones, smart phones, tablet computers, laptop computers, desktop computers, personal digital assistants, etc. FIG. 8 illustrates a model computing device in the form of a computer 810, which is capable of performing one or more computer-implemented steps in practicing the method aspects of the present invention. Components of the computer 810 may include, but are not limited to, a processing unit 820, a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI).

The computer 810 may also include a cryptographic unit 825. Briefly, the cryptographic unit 825 has a calculation function that may be used to verify digital signatures, calculate hashes, digitally sign hash values, and encrypt or decrypt data. The cryptographic unit 825 may also have a protected memory for storing keys and other secret data. In other embodiments, the functions of the cryptographic unit may be instantiated in software and run via the operating system.

A computer 810 typically includes a variety of computer readable media. Computer readable media can be any available media that can be accessed by a computer 810 and includes both volatile and nonvolatile media, removable and non-removable media. By way of example, and not limitation, computer readable media may include computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer 810. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared and other wireless media. Combinations of any of the above should also be included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 8 illustrates an operating system (OS) 834, application programs 835, other program modules 836, and program data 837.

The computer 810 may also include other removable/non-removable, volatile/nonvolatile computer storage media. By way of example only, FIG. 8 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

The drives, and their associated computer storage media discussed above and illustrated in FIG. 8, provide storage of computer readable instructions, data structures, program modules and other data for the computer 810. In FIG. 8, for example, hard disk drive 841 is illustrated as storing an OS 844, application programs 845, other program modules 846, and program data 847. Note that these components can either be the same as or different from OS 833, application programs 833, other program modules 836, and program data 837. The OS 844, application programs 845, other program modules 846, and program data 847 are given different numbers here to illustrate that, at a minimum, they may be different copies. A user may enter commands and information into the computer 810 through input devices such as a keyboard 862 and cursor control device 861, commonly referred to as a mouse, trackball or touch pad. Other input devices (not shown) may include a microphone, joystick, game pad, satellite dish, scanner, or the like. These and other input devices are often connected to the processing unit 820 through a user input interface 860 that is coupled to the system bus, but may be connected by other interface and bus structures, such as a parallel port, game port or a universal serial bus (USB). A monitor 891 or other type of display device is also connected to the system bus 821 via an interface, such as a graphics controller 890. In addition to the monitor, computers may also include other peripheral output devices such as speakers 897 and printer 896, which may be connected through an output peripheral interface 895.

The computer 810 may operate in a networked environment using logical connections to one or more remote computers, such as a remote computer 880. The remote computer 880 may be a personal computer, a server, a router, a network PC, a peer device or other common network node, and typically includes many or all of the elements described above relative to the computer 810, although only a memory storage device 881 has been illustrated in FIG. 8. The logical connections depicted in FIG. 8 include a local area network (LAN) 871 and a wide area network (WAN) 873, but may also include other networks 140. Such networking environments are commonplace in offices, enterprise-wide computer networks, intranets and the Internet.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. The modem 872, which may be internal or external, may be connected to the system bus 821 via the user input interface 860, or other appropriate mechanism. In a networked environment, program modules depicted relative to the computer 810, or portions thereof, may be stored in the remote memory storage device. By way of example, and not limitation, FIG. 8 illustrates remote application programs 885 as residing on memory device 881.

The communications connections 870 and 872 allow the device to communicate with other devices. The communications connections 870 and 872 are an example of communication media. The communication media typically embodies computer readable instructions, data structures, program modules or other data in a modulated data signal such as a carrier wave or other transport mechanism and includes any information delivery media. A "modulated data signal" may be a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Computer readable media may include both storage media and communication media.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A system for monitoring cardiac health of a user, the system comprising:
 a local sensing subsystem including a sensor patch configured to attach to the user, the sensor patch comprising:
  a substrate having first and second sections and configured to exhibit dielectric dispersion between the first and the second sections;
   wherein a positive electrode is carried by the first section of the substrate, and
   wherein a negative electrode is carried by the second section of the substrate; and
  a passive radio-frequency identification (RFID) transponder carried by the substrate, and comprising:
   a first antenna,
   a non-transitory and non-volatile storage medium in electrical communication with the first antenna,
   a load modulation switch in electrical communication with the first antenna, and
   a microcontroller in electrical communication with the first antenna and in data communication with both the storage medium and the load modulation switch;

a contactless interrogation subsystem including an interrogator device separated from the sensor patch, the interrogator device comprising:
   a second antenna in electrical communication with a power source and configured to wirelessly transmit electromagnetic radiation having a transmission frequency equal to a resonant frequency of the first antenna of the passive RFID transponder;
   a demodulator configured to measure a voltage amplitude of the electromagnetic radiation wirelessly transmitted by the second antenna; and
   a communications link in data communication with the demodulator and with at least one of a wired local area network (LAN) and a wireless LAN; and
a remote monitoring subsystem including a computing system comprising a processor for executing instructions stored in a non-transitory computer readable memory;
wherein the local sensing subsystem is adapted to perform at least one scan, wherein each scan is defined as use of the first antenna of the passive RFID transponder to inductively receive power for operating the passive RFID transponder of the sensor patch from the electromagnetic radiation wirelessly transmitted by the second antenna of the interrogator device, providing the microcontroller of the passive RFID transponder a cardiac activity signal from at least one of the positive and negative electrodes, operating the microcontroller to retrieve a location identifier from the storage medium of the passive RFID transponder, and operating the load modulation switch to alter the voltage amplitude of the electromagnetic radiation transmitted by the second antenna of the interrogator device to provide a cardiac event reading comprising the cardiac activity signal and the location identifier to the demodulator;
wherein the demodulator is adapted to receive the cardiac event reading from the load modulation switch and to operate the communications link to transmit the cardiac event reading; and
wherein the remote monitoring subsystem is adapted to execute the instructions to detect an arrhythmia from the cardiac event reading.

2. The system according to claim 1 wherein the first antenna of the passive RFID transponder is configured to inductively receive power from the electromagnetic radiation wirelessly transmitted by the second antenna of the interrogator device when the second antenna of the interrogator device is positioned a distance of less than six inches from the first antenna of the passive RFID transponder.

3. The system according to claim 1 wherein the remote monitoring subsystem is adapted to execute the instructions to create at least one of a location identifier and a patch identifier from the cardiac event reading, and to transmit, using the communications link, at least one of the location identifier and the patch identifier to the contactless interrogation subsystem;
   wherein the contactless interrogation subsystem is adapted to use the second antenna of the interrogator device to wirelessly transmit electromagnetic radiation conveying at least one of the location identifier and the patch identifier to the local sensing subsystem; and
   wherein the local sensing subsystem is adapted to use the microcontroller of the passive RFID transponder to receive at least one of the location identifier and the patch identifier from the first antenna of the passive RFID transponder and to store at least one of the location identifier and the patch identifier on the storage medium of the passive RFID transponder.

4. The system according to claim 1 wherein the local sensing subsystem is adapted to perform a plurality of scans in succession; wherein no two of the plurality of scans in succession occur at a scan rate of less than 868 MHz.

5. The system according to claim 1 wherein the sensor patch comprises a plurality of sensor patches each comprising a passive RFID transponder, the resonant frequency of the first antenna of the passive RFID transponders of each of the plurality of sensor patches being configured to be distinct from the respective resonant frequency of the first antenna of the passive RFID transponders of other sensor patches; wherein the second antenna of the interrogator device is adapted to wirelessly transmit electromagnetic radiation comprising a plurality of transmission frequencies such that at least one of the plurality of the transmission frequencies equals the respective resonant frequency of the first antenna of at least one of the passive RFID transponders of the plurality of sensor patches.

6. The system according to claim 5 wherein each of the plurality of transmission frequencies is characterized by a frequency selected from the group consisting of LF band (120-150 kHz) and HF band (13.56 MHz).

* * * * *